US010245349B2

(12) United States Patent
Brahm

(10) Patent No.: US 10,245,349 B2
(45) Date of Patent: *Apr. 2, 2019

(54) BIRTH TISSUE MATERIAL AND METHOD OF PREPARATION

(71) Applicant: BioDlogics, LLC, Cordova, TN (US)

(72) Inventor: Timothy R. Brahm, Germantown, TN (US)

(73) Assignee: BioDlogics, LLC, Cordova, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,415

(22) Filed: Sep. 16, 2015

(65) Prior Publication Data
US 2016/0082152 A1    Mar. 24, 2016

Related U.S. Application Data

(60) Continuation of application No. 14/557,967, filed on Dec. 2, 2014, now abandoned, which is a division of application No. 13/664,857, filed on Oct. 31, 2012, now Pat. No. 8,932,805.

(60) Provisional application No. 61/553,336, filed on Oct. 31, 2011.

(51) Int. Cl.
| A61L 27/36 | (2006.01) |
| A01N 1/02 | (2006.01) |
| A61K 35/50 | (2015.01) |
| A61K 45/06 | (2006.01) |
| A61K 47/46 | (2006.01) |
| A61B 17/42 | (2006.01) |
| A61M 1/00 | (2006.01) |
| A61M 25/10 | (2013.01) |
| C12N 5/073 | (2010.01) |
| A61L 27/54 | (2006.01) |
| A61L 27/58 | (2006.01) |

(52) U.S. Cl.
CPC ........ *A61L 27/3604* (2013.01); *A01N 1/0221* (2013.01); *A61B 17/4208* (2013.01); *A61K 35/50* (2013.01); *A61K 45/06* (2013.01); *A61K 47/46* (2013.01); *A61L 27/54* (2013.01); *A61L 27/58* (2013.01); *A61M 1/008* (2013.01); *A61M 25/1011* (2013.01); *C12N 5/0605* (2013.01); *A61L 2300/412* (2013.01); *A61L 2300/43* (2013.01); *A61L 2300/438* (2013.01); *A61L 2430/34* (2013.01)

(58) Field of Classification Search
CPC .................................................. C12N 5/0605
See application file for complete search history.

(56) References Cited

U.S. PATENT DOCUMENTS

| 3,409,016 A | 11/1968 | Foley |
| 5,036,056 A | 7/1991 | Kludas |
| 6,152,142 A | 11/2000 | Tseng |
| 6,326,019 B1 | 12/2001 | Tseng |
| 7,727,550 B2 | 6/2010 | Siegal et al. |
| 7,871,646 B2 | 1/2011 | Ghinelli |
| 8,071,135 B2 | 12/2011 | Liu et al. |
| 8,153,162 B2 | 4/2012 | Tseng |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,278,102 B2 * | 10/2012 | Ennis ............... A01N 1/02 424/583 |
| 8,956,862 B2 | 2/2015 | Pal et al. |
| 2003/0054331 A1 | 3/2003 | Fraser et al. |
| 2004/0057938 A1 | 3/2004 | Ghinelli |
| 2007/0021762 A1 | 1/2007 | Liu et al. |
| 2007/0031471 A1 | 2/2007 | Peyman |
| 2007/0292401 A1 | 12/2007 | Harmon et al. |
| 2011/0206776 A1 | 8/2011 | Tom et al. |
| 2012/0141595 A1 | 6/2012 | Tseng et al. |
| 2013/0287741 A1 | 10/2013 | Stilwell et al. |
| 2014/0017280 A1 | 1/2014 | Daniel et al. |
| 2014/0037598 A1 | 2/2014 | Jansen et al. |
| 2014/0050788 A1 | 2/2014 | Daniel et al. |
| 2014/0052247 A1 | 2/2014 | Daniel et al. |

FOREIGN PATENT DOCUMENTS

| EP | 0285370 | 10/1988 |
| WO | WO-2006/094247 | 1/2006 |
| WO | WO-2009/052132 | 1/2009 |
| WO | WO-2012/003377 | 1/2012 |

OTHER PUBLICATIONS

Sheha et al. J of American Science, 2010, 6(11):427-433.*
Bonci et al. European J of Ophthalmology, 2005, 15(4):441-445.*
Hennerbichler et al. Cell Tissue Banking, 2007, 8:1-8.*
Avanzi, et al., "Susceptibility of human placenta derived mesenchymal stromal/stem cells to human herpes virus infection", PLOS One, vol. 8, No. 8 (Aug. 2013), pp. 1-14.
Brooke et al., "Manufacturing of human placenta-derived mesenchymal stem cells for clinical trials", British Journal of Haematology, vol. 144 (2008), pp. 571-579.
Fuller, et al., "Stem cells", Clinical Applications of Cryobiology, (2000), pp. 127-134.
Gavin, "Histopathology of "fresh" human aortic valve allografts", Thorax, vol. 28 (1973), pp. 482-487.
Haimov-Kochman et al. "Modification of the standard trizol-based technique improves the integrity of RNA isolated from RNase-rich placental tissue", Clinical Chemistry, vol. 52, No. 1 (2006), pp. 159-160.
Jaattela, et al., "Demonstration of tumor necrosis factor in human amniotic fluids and supernatants of placental and decidual tissues", Laboratory Investigation, vol. 58, No. 1 (1998), pp. 48-52.

(Continued)

Primary Examiner — Bin Shen
(74) Attorney, Agent, or Firm — Brinks Gilson & Lione

(57) ABSTRACT

A method of treating a soft tissue defect in or on the body of a patient is provided. A placental construct for treatment of a disease or condition is also provided. The placental construct includes a therapeutically effective amount of a birth tissue material.

8 Claims, 16 Drawing Sheets

(56) References Cited

OTHER PUBLICATIONS

Kagan, "The skin bank", Chapter 15 in Total Burn Care (2012), pp. 199-208.
Liu, et al., "The use of type I and type II injectable human collagen for dermal fill: 10 years of clinical experience in China", Seminars in Plastic Surgery, vol. 19, No. 3 (2005), pp. 241-250.
Parolini, et al., "Concise review: Isolation and characterization of cells from human term placenta: Outcome of the first international workshop on placenta derived stem cells", Stem Cells, vol. 26 (2008), pp. 300-311.
Sabapathy, et al., "Long-term cultured human term placenta-derived mesenchymal stem cells of maternal original displays plasticity", Stem Cells International, vol. 2012 (2012), pp. 1-11.
Scheffer et al., "Amniotic membrane transplantation with or without limbal allografts for corneal surface reconstruction in patients with limbal stem cell deficiency", Archives of Opthalmology, vol. 116, No. 4 (1998), pp. 431-441.
Federal Register, "Human cells, tissues and cellular and tissue-based products; establishment registration and listing", Federal Register, vol. 66, No. 13 (Jan. 19, 2001), pp. 5447-5469.
American Association of Tissue Banks, "Standards for Tissue Banking", 13$^{th}$ edition, published Feb. 29, 2012, p. 58.
Court Case No. CV-15-00095-PHX-SRB, "Order Staying all proceedings pending reexamination of U.S. Pat. No. 8,932,805", *Amnio Technology, LLC* v. *BioDlogics, LLC*, filed Sep. 30, 2015.
Electronic Code of Federal Regulations, §1271.220 "Processing and process controls", downloaded Nov. 18, 2015.

\* cited by examiner

| | BATCH VOLUME AND ALIQUOT FILL CALCULATION | | | | | |
|---|---|---|---|---|---|---|
| A. | AMNION WEIGHT (AW) | | | | | |
| | | | Amnion Weight (g) | | (AW) _____ g | |
| B. | AMNION ALLOWABLE ALIQUOTS (AA) | | | | | |
| | (AW) _____ g    /    0.03 g    = | | | | (AA) _____ | |
| | Amnion Weight(g)    Minimum Amnion(g) per 1mL aliquot | | | | | |
| C. | CELL COUNT | | | | | |
| | Amniotic Fluid Volume (mL) (A) | Total Cells Counted (5 Large Squares) (B) | Average Cells / Square (C) (C = B / 5) | Dilution Factor (D) | Total Cell Density (E) (Cells/mL) (E = C x D x 10⁴) | Total Cells (TC) (TC = E x A) |
| | (A) | (B) | (C) | (D) | (E) | (TC) |
| D. | ALIQUOT CELL DENSITY (ALIQUOT = 1 mL) | | | | | |
| | (TC) _____   /   (AA) _____   =      (CD) _____ ml | | | | | |
| | Total Cells        Amnion Allowable Aliquot          Aliquot Cell Density | | | | | |
| E. | BULK PRODUCT VOLUME (BV) | | | | | |
| | (AA) _____ = (BV) _____ | | | | | |
| F. | LOT VIAL FILL CALCULATIONS | | | | | |
| | Bulk Product Volume    (BV) | | = | | | mL |
| | Actual Vial Target 0.25 mL = | | X 0.25 = | | | mL |
| | Actual Vial Target 0.50 mL = | | X 0.50 = | | | mL |
| | Actual Vial Target 1.25 mL = | | X 1.25 = | | | mL |
| | TOTAL VIAL Target | | Total Vial Fill Volume* | | | mL |
| | * Total Vial Fill Volume Must be ≤ Bulk Product Volume | | | | | |

FIG. 2

| | SOLUTION CALCULATIONS | | |
|---|---|---|---|
| | SUSPENSION SOLUTIONS (SS) CALCULATIONS | | |
| a) | (BV) _____mL  =  (SS) _____mL | | |
| | Bulk Product Volume (mL) | | Total Suspension Solution Volume (mL) |
| | Cell Suspension Solution (CS) | | |
| i) | _____(SS) / 2 = | | _____mL (CS) |
| | Component Description | Volume Calculation | Volume Required |
| | Plasma Lyte-A Injection (pH 7.4) | (CS)  x  0.91  = | mL |
| | Human Albumin 25% Solution | (CS)  x  0.09  = | mL |
| | Amnion Suspension Solution (AS) | | |
| ii) | _____(SS) / 2 = | | _____mL (AS) |
| | Component Description | Volume Calculation | Volume Required |
| | Plasma Lyte-A Injection (pH 7.4) | (AS)  x  0.44  = | mL |
| | Human Albumin 25% Solution | (AS)  x  0.36  = | mL |
| | DMSO (Dimethyl Sulfoxide), USP | (AS)  x  0.20  = | mL |
| | AMNION CONTROL RATE FREEZE SOLUTION   =   50 mL | | |
| | Component Description | Volume Calculation | Volume Required |
| b) | Plasma Lyte-A Injection (pH 7.4) | 50 ml  x  0.44  = | 22 mL |
| | Human Albumin 25% Solution | 50 ml  x  0.36  = | 18 mL |
| | DMSO (Dimethyl Sulfoxide), USP | 50 ml  x  0.20  = | 10 mL |

FIG. 3

BIRTH TISSUE MATERIAL AND METHOD OF PREPARATION

CROSS-REFERENCE TO RELATED APPLICATIONS

The present application is a continuation of U.S. Ser. No. 14/557,967 filed Dec. 2, 2014 which is a divisional of U.S. Ser. No. 13/664,857, now U.S. Pat. No. 8,932,805, filed Oct. 31, 2012 which claims the benefit of U.S. provisional application No. 61/553,336 filed Oct. 31, 2011, the contents of each are incorporated herein by reference in their entirety.

FIELD OF THE INVENTION

Methods of preparing a human birth tissue material are provided. A placental construct for treatment of a disease or condition is also provided. A kit including at least one placental construct and at least one structural carrier is provided. A catheter for recovering amniotic fluid is also provided.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, associated membranes (chorionic membrane and amniotic membrane), other gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

Various manufacturing processes have also been employed to create wound coverings composed of amniotic membrane, chorionic membrane, or intact amniotic and chorionic membranes recovered aseptically from human birth tissue after elective Cesarean surgery. There remains a need, however, for membranes that are uniquely processed and combined with components of the amniotic fluid to enhance the tissue's physical properties and to provide a material that can aid in the repair of bone and soft tissue.

Catheters are tube-like devices which are inserted into a portion of a person's body in order to transport liquids, gases, and sometimes semisolids, into or out of that portion of the body. For instance, urinary catheters are used to transport urine collected in the bladder out of the body via the urinary tract. Other types of catheters, such as gastronomy devices, transport fluids into and out of various segments of the gastrointestinal system, primarily the stomach.

In order to provide a means of retaining the catheter within the body, inflatable bag catheters were introduced many years ago. Foley (U.S. Pat. No. 3,409,016) taught an elongated catheter having a secondary lumen for inflating a retention balloon at a distal end of the catheter once the distal end is positioned within the body. Such catheters are now generally referred to as "Foley" catheters out of respect for the contribution made by Dr. Foley. Improvements on Foley catheters continue to find their way into the market place today. Thus, there remains a need for an improvement upon a Foley catheter whereby a dual balloon system allows for the sterile recovery of fluid while sealing off a pressurized biological membrane(s) to prevent fluid leakage and membrane tear and/or rupture.

SUMMARY OF THE INVENTION

Placental constructs for treatment of a disease or condition are provided. According to one aspect, the placental construct includes a therapeutically effective amount of a birth tissue material. The birth tissue material includes at least one morselized placental tissue component and an amniotic fluid composition. According to one embodiment, the at least one placental tissue component is amniotic membrane.

According to another aspect, a placental construct for treatment of a disease or condition is provided that includes a therapeutically effective amount of a birth tissue material prepared by a process including the steps of:

(a) recovering placental tissue components and amniotic fluid from a seronegative, healthy human via cesarean section or vaginal delivery;

(b) subjecting the placental tissue components to cryopreservation;

(c) morselizing the cryopreserved placental tissue components;

(d) homogenizing the morselized placental tissue components in a tissue suspension solution to form a tissue suspension;

(e) homogenizing the tissue suspension with an amniotic fluid composition to form a bulk tissue product; and (f) cryofreezing the bulk tissue product to form the human birth tissue material.

According to another aspect, a placental construct for treatment of a disease or condition is provided that includes a therapeutically effective amount of a birth tissue material. The birth tissue material includes a tissue suspension comprising morselized placental tissue components homogenized in a tissue suspension solution and an amniotic fluid composition comprising a cell suspension solution. According to one embodiment, the tissue suspension solution comprises Plasma Lyte-A, human albumin solution, and dimethyl sulfoxide. According to one embodiment, the tissue suspension solution comprises about 44% volume of Plasma Lyte-A, about 36% volume of human albumin 25% solution, and about 20% volume of dimethyl sulfoxide. According to one embodiment, the cell suspension solution comprises Plasma Lyte-A and human albumin solution. According to one embodiment, the cell suspension solution comprises about 91% volume of Plasma Lyte-A and about 9% volume of human albumin 25% solution.

According to one embodiment, the placental constructs as provided herein may be used for bone or soft tissue repair, bone or soft tissue reconstruction, bone or soft tissue augmentation, bone or soft tissue sealing, or soft tissue cosmetic applications.

According to one embodiment, the placental constructs as provided herein are used to treat a soft tissue defect or a bone void. According to one embodiment, the soft tissue defect is a persistent wound such as, for example, a diabetic ulcer, decubitus ulcer, venous leg ulcer, arterial leg ulcer, or cutaneous ulcer. According to one embodiment, the soft tissue defect is tendinitis or tendinosis.

According to one embodiment, the placental constructs as provided herein are applied directly into or onto a site to treat a soft tissue defect or bone void.

According to one embodiment, the placental constructs as provided herein are formulated in an injectable formulation.

According to one embodiment, the placental constructs as provided herein include birth tissue material that is cryopreserved prior to use.

According to one embodiment, the placental constructs as provided herein also include one or more structural carriers such as, for example, an amniotic membrane and/or chorionic membrane, a soft tissue allograft, a bone allograft, or platelet rich plasma.

According to one embodiment, the placental constructs as provided herein are also include one or more bioactive agents such as, for example, physiologically compatible minerals, growth factors, antibiotics, chemotherapeutic agents, antigens, antibodies, enzymes, vectors for gene delivery, or hormones.

According to another aspect, a kit is provided that includes at least one placental construct as provided herein and at least one additional structural carrier. According to one embodiment, the structural carrier is a placental membrane construct, soft tissue allograft, bone allograft, or platelet rich plasma. According to one embodiment, the kit further includes instructions for use thereof.

BRIEF DESCRIPTION OF THE DRAWINGS

FIG. 2 provides a batch volume and fill calculation sheet according to one embodiment;

FIG. 3 provides a solution calculation sheet according to one embodiment;

DETAILED DESCRIPTION OF THE INVENTION

Figure 1:
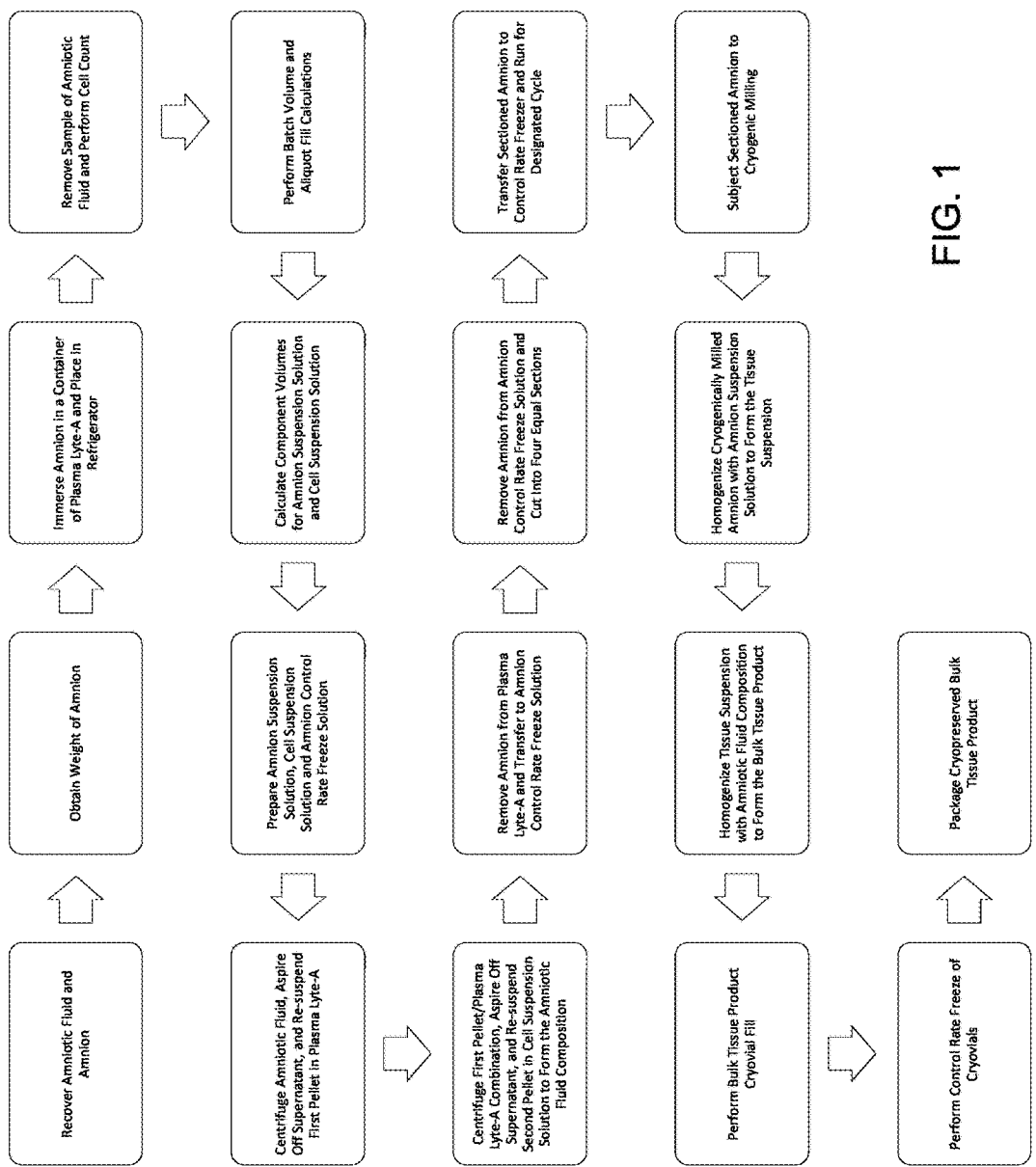
FIG. 1 is schematic providing an overview of the method of preparing a human birth tissue material according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human birth tissue" encompasses one or more of the components of the placental organ including, but not limited to, the placental globe, the umbilical cord, the chorionic membrane, the amniotic membrane, other gelatins, cells, and extracellular material, and amniotic fluid.

As used herein, "placental tissue components" encompasses one or more of the tissue components of the placental organ including, but not limited to, the placental globe, the umbilical cord, the chorionic membrane, the amniotic membrane, and other gelatins, cells and extracellular material.

As used herein, the term "amnion" and "amniotic membrane" are used interchangeably.

As used herein, the term or phrase "surgical site" refers to the exact location of a surgery or a location sufficiently near a surgical procedure on a patient.

Methods for preparing human birth tissue material to produce a construct having improved properties for use in bone and soft tissue repair are provided. One embodiment of a method of preparing birth tissue material is provided in the schematic of FIG. 1. The method of preparing a human birth tissue material includes the step of recovering placental tissue components and amniotic fluid from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

Once recovered, one or more of the placental tissue components can be removed via a sterile saline solution rinse, blunt dissection, scalpel, or a combination thereof, if necessary. According to one embodiment, the placental globe, umbilical cord, chorionic membrane, and other gelatins, fluids, cells and extracellular matrix are removed and discarded, leaving the amniotic membrane for further processing. In a preferred embodiment, the human birth tissue material is subject to the method of preparation described herein no more than four hours after recovery to preserve cell viability.

The retained placental tissue components can be placed in a sterile transport solution after aseptic recovery. The sterile transport solution is used to provide an advantageous medium to the natural function of the placental tissue components prior to processing. For example, calcium-rich water can be used as the sterile transport solution to provide a medium to drive undifferentiated cells to become osteogenic when implanted. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 10% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

Amniotic fluid can be placed in a sterile container after aseptic recovery. In a preferred embodiment, a cell count is performed on the amniotic fluid using methods commonly known in the art (e.g., hemocytometer). The amniotic fluid is preferably mixed thoroughly before a sample is taken to ensure that the sample is representative of the number of cells dispersed throughout the amniotic fluid. Additionally, an appropriate dilution of the mixture with regard to the number of cells to be counted can be utilized. The total cell count per milliliter can then be calculated. In another embodiment, a cell counter can be used to determine total cell count per milliliter of fluid. After the cell count is determined, a requisite cell suspension solution volume can be calculated and prepared. The cell suspension volume may be calculated from predetermined requirements for the minimum starting gram weight of tissue per mL of bulk tissue product. In an alternate embodiment, the cell suspension volume may be calculated from predetermined requirements for the minimum number of amniotic fluid cells per 1.0 mL aliquot of bulk tissue product. In one embodiment, the cell suspension solution includes typically about 91% volume of Plasma Lyte-A and typically about 9% volume of human albumin 25% solution.

In a preferred embodiment, after the cell count is completed, an amniotic fluid composition is prepared according to the following steps. Particles in the amniotic fluid are separated from the liquid component of the amniotic fluid using centrifugation. The resulting, separated particles are referred to as "pellets." The separation of particles from the liquid component of the amniotic fluid may occur by any art-recognized method including sedimentation or microfiltration. In a preferred embodiment, the amniotic fluid is evenly aliquoted into sterile conical centrifuge tubes. The amniotic fluid can be distributed in equal amounts in as many tubes as necessary for the volume recovered. The amniotic fluid can be centrifuged at 200 rpm to 15,000 rpm for a period of up to 30 minutes at ambient temperature. In one embodiment, the amniotic fluid is centrifuged at approximately 1410 rpm (400×gravity [RCF]) for a period of 10 minutes at ambient temperature. Using a sterile pipette, the supernatant can be aspired from each tube and discarded. An isotonic solution can be used to re-suspend each pellet and bring the volume of each tube up to a predetermined amount. In one embodiment, the isotonic solution is Plasma Lyte-A. The pellet/isotonic solution combination can be centrifuged at 200 rpm to 15,000 rpm for a period of up to 30 minutes at ambient temperature. In one embodiment, the pellet/isotonic solution combination is centrifuged at approximately 1410 rpm (400×g [RCF]) for a period of 10 minutes at ambient temperature. Using a sterile pipette, the second supernatant can be aspired from each tube and discarded. Each second pellet can be re-suspended in a cell suspension solution of a predetermined amount to form the amniotic fluid composition. In one embodiment, the cell suspension solution includes Plasma Lyte-A and human albumin 25% solution. In a preferred embodiment, the cell suspension solution includes typically about 91% volume of Plasma Lyte-A and typically about 9% volume of human albumin 25% solution. The cells in each tube can be thoroughly suspended by using a vortex mixer for a minimum of three seconds. Immediately thereafter, the contents of each tube are homogenized with a cell suspension solution to form the amniotic fluid composition. In a preferred embodiment, the cell suspension solution includes typically about 91% volume of Plasma Lyte-A and typically about 9% volume of human albumin 25% solution.

In one embodiment, the discarded first and second supernatant from the aforementioned amniotic fluid composition preparation steps are further precipitated using dialysis equipment or micropore/nucleopore filters. Alternately, the first and second supernatant can be further precipitated by pipetting the supernatants onto sterile wax paper, heating the contents to quickly evaporate the liquid, and then adding the remaining material back into the final amniotic fluid composition. This method allows for the removal of the extraneous liquid, while maximizing the cells, proteins and other particles otherwise discarded in the first and second supernatants. The remaining material precipitated from the first and second supernatants can be homogenized with the amniotic fluid composition.

After the amniotic fluid composition is generated, a second cell count can be performed on a representative sample using a hemocytometer, a cell counter, or any other method commonly known in the art. The amniotic fluid preparation can be stored at typically about 1-10° C. for a period of up to 24 hours pending further processing.

A predetermined percentage of the amniotic fluid composition (representative sample) can be retained for testing and not included in the final bulk product. This representative sample can be retained for analysis and comparison to the cells in the final bulk product to discern any deleterious effects on the amniotic fluid cells, particularly the effects of the cryoprotectant(s) on the amniotic fluid cells in the final bulk product and/or the effects of cleaning, processing, freezing and thawing on the amniotic fluid cells.

Simultaneous with the initial cell count of the amniotic fluid, the weight of the placental tissue components can be determined. Thereafter, the placental tissue components can be transferred aseptically to a sterile dish containing Plasma Lyte-A and stored in a quarantine refrigerator pending further processing.

After the weight of the placental tissue components is determined, a requisite tissue suspension solution volume can be calculated and prepared based on predetermined requirements for the minimum starting gram weight of tissue per mL of bulk tissue product. In one embodiment, the tissue suspension solution comprises Plasma Lyte-A, human albumin 25% solution, and dimethyl sulfoxide. In a preferred embodiment, the tissue suspension solution comprises: typically about 44% volume of Plasma Lyte-A, typically about 36% volume of human albumin 25% solution, and typically about 20% volume of dimethyl sulfoxide.

In one embodiment, the total number of final product units can be calculated based on predetermined requirements for: (1) the minimum starting tissue gram weight per mL of bulk tissue product; and (2) the minimum number of amniotic fluid cells per 1.0 mL aliquot of bulk tissue product. In a preferred embodiment, the total number of final product units can be calculated based on predetermined requirements for the minimum starting tissue gram weight per mL of bulk tissue product. In one embodiment, the final product vials can be of various volumes such as, for example, 0.25 mL, 0.50 mL, 1.25 mL, or any other volume as contemplated by one of ordinary skill in the art.

In one embodiment, the placental tissue components include amniotic membrane. In another embodiment, the placental tissue components include one or more components selected from the group consisting of amniotic membrane, chorionic membrane, Wharton's jelly, umbilical cord tissue, placental globe, and other gelatins, other cells and extracellular matrix from placental tissue components. The placental tissue components can them be placed in a sterile dish containing Plasma Lyte-A until further processing.

The placental tissue components can be removed from the Plasma Lyte-A and cryopreserved according to methods commonly used in the art. The placental tissue components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

After cryopreservation, the placental tissue components are subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. In one embodiment, the total number of final product units can be calculated based on predetermined requirements for: (1) the minimum tissue gram weight after morselization per mL of bulk tissue product; and (2) the minimum number of amniotic fluid cells per 1.0 mL aliquot of bulk tissue product. In an alternate embodiment, the total number of final product units can be calculated based on predetermined requirements for the minimum tissue gram weight after morselization per mL of bulk tissue product.

After morselization, the milled placental tissue components can be combined with the tissue suspension solution to form a tissue suspension. In one embodiment, the tissue suspension solution includes Plasma Lyte-A, human albumin 25% solution, and dimethyl sulfoxide, which is used immediately to prepare the final bulk tissue product. In a preferred embodiment, the tissue suspension solution comprises typically about 44% volume of Plasma Lyte-A, typically about 36% volume of human albumin 25% solution, and typically about 20% volume of dimethyl sulfoxide, which is used immediately to prepare the final bulk tissue product. In an alternate embodiment, the tissue suspension solution includes typically about 44% volume of Plasma Lyte-A and typically about 36% volume of human albumin 25% solution. The 20% volume of dimethyl sulfoxide is purposefully withheld pending final combination of the bulk tissue product. In this alternate embodiment, the milled tissue suspension (without dimethyl sulfoxide) can be stored at about 1-10° C. for a period of up to about 24 hours, pending further processing. In the alternate embodiment, the 20% volume of dimethyl sulfoxide can be added to the tissue suspension immediately prior to final bulk tissue product manufacture.

Bulk tissue product can be manufactured by homogenizing the amniotic fluid composition and the tissue suspension. Both the amniotic fluid composition and the tissue suspension can be vortexed for no less than about three seconds prior to combination. In a preferred embodiment, the bulk tissue product can be homogenized using a laboratory homogenizer mixer, followed by continuous mixing with magnetic stirrers. Immediately thereafter, the bulk tissue product can be placed on cold packs and individual, empty cryovials can be filled with the bulk tissue product. In one embodiment, the final product vials can be of various volumes such as, for example, 0.25 mL, 0.50 mL, 1.25 mL, or any other volume as contemplated by one of ordinary skill in the art. Cryopreservation of the final bulk tissue product vials can be achieved through control-rate freezing by methods commonly known in the art.

Representative samples from the beginning, middle, and end of the cryovial fill cycle can be removed from the final product count for quality control testing, including, but not limited to, bioburden testing, mycoplasma DNA by polymerase chain reaction, and bacterial endotoxin test (Limulus Ameboycte Lysate). Representative samples from the beginning, middle, and end of the cryovial fill cycle can be removed from the final product count to store for future testing should the need arise.

A placental construct is provided for treatment of a disease or condition, including bone or soft tissue repair, bone or soft tissue reconstruction, bone or soft tissue augmentation, bone or soft tissue sealing, or soft tissue cosmetic applications.

The placental construct includes a therapeutically effective amount of a birth tissue material prepared according to the methods set forth herein. In a preferred embodiment, the placental construct is administered by a user (i.e., medical professional) either through injection or by direct application over the chosen site. Modes of administration may include, but not be limited to: intramuscular, subcutaneous, intraperitoneal, percutaneous, soft tissue injection, surgical placement, arthroscopic placement, intravenous, intravascular, intracerebral, transdermal, topical or mucosal. Most preferred methods result in localized administration of the inventive composition to the site or sites of tissue defect. Any administration may be a single application of the placental construct or multiple applications. Administrations may be to single site or to more than one site in the individual to be treated. Multiple administrations may occur essentially at the same time or separated in time.

In one embodiment, the disease or condition that is treated via the present placental construct is a bone void. The invention provides methods for sealing, filling and/or otherwise treating a bone void within the body of a patient. In some embodiments, the methods of the invention comprise injecting or otherwise administering a placental construct of the invention to a patient to fill a void within the body of the patient. For example, a placental construct can be administered to the patient in the area where the void is located. The term "void" is intended to encompass any undesirable hollow space created by aging, disease, surgery, congenital abnormalities, or a combination thereof. For example, a void may be created following the surgical removal of a tumor or other mass from a bone of a patient. Non-limiting examples of bone voids which may be filled with a placental construct of the invention include a fissure, fistula, cyst, lesion, osseus, traumatic or surgically created defect, cortical or segmental defect, atrophic and/or oligotrophic non-union, or any other undesirable hollow space in any bone of the patient's body.

In a preferred embodiment, the placental construct can aid in guided bone regeneration by injecting the placental construct into a damaged or diseased bone region for repair. The placental construct can be used alone, or in combination with one or more additional structural carriers, including, but not limited to, a placental membrane construct (e.g., amniotic membrane wound covering), a soft tissue allograft, a bone allograft (e.g., FDBA), or platelet rich plasma. The placental construct can be used alone, or in combination with one or more additional bioactive agents such as physiologically compatible minerals, growth factors, antibiotics, chemotherapeutic agents, antigen, antibodies, enzymes, vectors for gene delivery and hormones.

In one embodiment, the disease or condition that is treated via the placental construct is a soft tissue defect. The invention provides methods for sealing, filling and/or otherwise treating a soft tissue defect in or on the body of a patient. In some embodiments, the methods of the invention comprise injecting or otherwise administering a placental construct of the invention to a patient to treat a soft tissue defect within the body of the patient. In one embodiment, the soft tissue defect is a persistent wound including at least one diabetic ulcer, decubitus ulcer, venous leg ulcer, arterial leg ulcer, cutaneous ulcer or a combination thereof. In one embodiment, the soft tissue defect is tendinitis or tendinosis. Other soft tissue defects to be treated by the present placental construct further include, for example, conditions of skin (e.g., ischemic wounds, scar revision or the treatment of traumatic wounds, severe burns, surgical wounds such as those associated with the excision of skin cancers); cosmetic conditions (e.g., those involving repair, augmentation, or beautification); muscle diseases (e.g., congenital myopathies; myasthenia gravis; inflammatory, neurogenic, and myogenic muscle diseases); conditions of connective tissues such as tendons and ligaments, including, but not limited to, a periodontal ligament and anterior cruciate ligament; and conditions of organs and/or fascia (e.g., the bladder, intestine, pelvic floor). The placental construct can be used alone, or in combination with one or more additional structural carriers, including, but not limited to, placental membrane constructs, soft tissue allografts or platelet rich plasma. The placental construct can be used alone, or in combination with one or more additional bioactive agents such as physiologically compatible minerals, growth factors, antibiotics, chemotherapeutic agents, antigen, antibodies, enzymes, vectors for gene delivery and hormones.

The placental construct of the present invention has particular utility in dental applications, e.g., periodontal surgery, periodontal ligament reattachment, gingival recession recovery, connective tissue grafting, sinus lifts, socket preservation and augmentation, buccal defect treatment, ridge augmentation, guided bone regeneration, and guided tissue regeneration. The invention encompasses the use of the placental construct of the present invention to promote enhanced therapeutic utility and enhanced clinical parameters which include, but are not limited to, probing pocket depth, probing attachment depth, bone quality classification (density/volume) and gingival pocket recession.

In other embodiments, the wound covering of the present invention can be manufactured as an injectable solution, powder, gel or putty. In one embodiment, the gel or putty carrier could be achieved through collagen extracted from the placental globe.

Also provided herein is a kit including at least one placental construct and at least one additional structural carrier. Such kits can include a package that is compartmentalized to receive one or more containers, each of the container(s) including one of the separate elements include in the kit described herein. Suitable containers include, for example, bottles, vials, syringes, and test tubes. The containers can be formed from a variety of materials such as glass or plastic. The kit is appropriately preserved up until and during shipment to a distributor or medical facility. The structural carrier is any acceptable carrier such as, for example, a placental membrane construct (e.g., amniotic membrane wound covering), soft tissue allograft, bone allograft (e.g., FDBA), platelet rich plasma, or a combination thereof. The kit additionally includes at least one set of instructions for the end user (i.e., medical professional).

Figure 16:
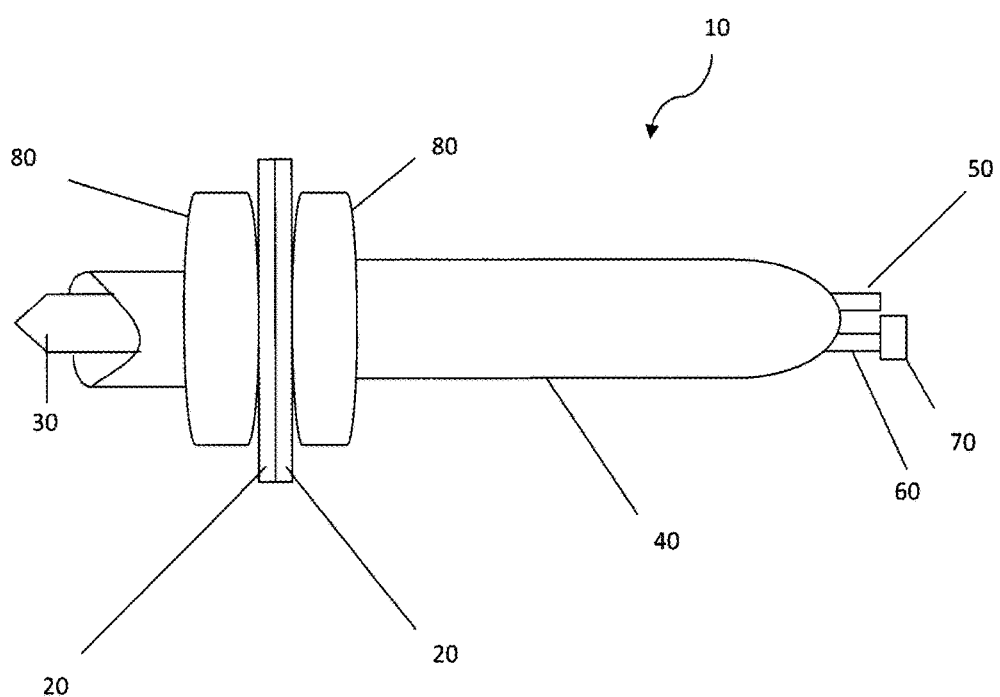
FIG. 16 illustrates a catheter according to one embodiment of the present invention.

Obtaining amniotic fluid from a mother can be achieved with an instrument that is an improvement upon existing catheters in the art. The present device 10 is shown in FIG. 16 and provides a dual balloon system to seal off both sides of the membranes 20 (e.g., amnion and chorion membranes), which is not possible with a traditional catheter, such as a Foley catheter, which provides only one balloon. The flexible tube 40 encompasses a first lumen 50 and a second lumen 60. The first lumen 50 contains the cannulated trocar head 30 capable of passing through the membranes 20. The first lumen 50 is open at both the proximal and distal ends, allowing amniotic fluid to drain into a sterile collection container (not shown). The second lumen 60 has a valve 70 and connects internally to two balloons 80.

In use, before the baby is removed from the womb, the user (e.g., medical professional) can make a small perforation using the cannulated trocar head on the fetal sac that includes the amnion and chorion membranes. A first balloon can be positioned to inflate from the second lumen on the distal side of the chorion membrane. A second balloon can be positioned to inflate from the second lumen on the proximal side of the amniotic membrane. After the cannulated trocar head penetrates the membranes, the cannulated trocar head can be withdrawn through the first lumen. At a certain point in withdrawal of the cannulated trocar head, the first and second balloons can be triggered to inflate via the valve. The device can use gravity, womb pressure, or vacuum suction to inflate the balloons after proper positioning of the device. Alternatively, the balloons can be inflated with sterile water after proper positioning of the device. Inflation of the dual balloon system simultaneously prevents the device from slipping out of the fetal sac, in addition to sealing the perforations caused by the entry of the device into the amnion and chorion membranes to prevent amniotic fluid loss. Furthermore, inflation of the balloons prevents further tearing or rupturing of the membranes and prohibits material blood from entering into in the fetal sac (i.e., prohibits cross-contamination of material blood and amniotic fluid).

The device can be manufactured from any appropriate materials capable of sterilization, such as silicone rubber, natural rubber, or plastic. The anatomy of the fetal sac is particularly suited for the present dual balloon system because pressure on both the proximal side of the amniotic membrane and the distal side of the chorionic membrane is required to recover amniotic fluid from the pressurized womb.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

EXAMPLES

The placental construct as utilized in the subsequent examples was prepared according to the method of FIG. 1, the details of which are herein provided.

Human birth tissue was obtained from a seronegative, healthy mother via Cesarean section. To maximize the overall quality of the donated tissue, a recovery technician was present in the operating room during the donor's Cesarean section to assist the surgical team with recovery, treatment and handling of the birth tissue. The donor was surgically prepped and draped per AORN standards prior to the Cesarean section procedure. The recovery technician prepared the recovery site by establishing a sterile field on a back table in the operating room.

Amniotic fluid was recovered according to the following procedures provided herein. The physician's assistant cleared all maternal blood from the surgical site. A suction cannula was positioned directly above the intended amnion/chorion membrane incision site. Using the smallest appropriate incision, the amniotic and chorionic membranes were breached, releasing the amniotic fluid into the suction cannula. Avoiding maternal blood, the physician's assistant suctioned as much amniotic fluid volume as possible into a sterile suction canister. Immediately following recovery, the sterile suction canister was transferred to the sterile back table. The recovery technician examined the amniotic fluid for the presence of visible blood. After noting that no visible blood was present, the recovery technician aseptically transferred the amniotic fluid to a sterile Nalgene jar and performed swab cultures. The recovery technician secured the lid on the Nalgene jar to which the appropriate identification was affixed.

Following delivery of the baby, the physician's assistant placed the human birth tissue en-bloc into a sterile basin. Maintaining sterility, the basin was transferred to the recovery technician onto the sterile field on the back table. Beginning at the amnion/chorion membrane surgical incision site, the recovery technician used blunt dissection to separate the chorionic membrane from the amniotic membrane, using care not to tear the amniotic membrane. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 mL of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed.

The Nalgene jar containing the amniotic fluid and the plastic transport container containing the amniotic membrane were placed in a qualified shipping container with an appropriate amount of wet ice to maintain refrigerated temperatures. The validated box arrived at the processing facility approximately one hour following recovery and was immediately inspected per standard operating procedures and placed in refrigerated temperatures (1-10° C.).

Processing was performed on a sterile field using aseptic technique in a validated cleanroom at the processing facility less than four hours after the recovery was completed. All manufacturing steps were recorded concurrently by a circulating technician on a designated processing record.

Amniotic Membrane Preparation

The amniotic membrane was removed from the plastic transport container and outer bag. The inner bag containing the amniotic membrane was aseptically passed onto a sterile field. Approximately 35 mL of the sterile transport solution was aspirated out of the bag utilizing a sterile pipette. Subsequently, the sample was transferred to a sterile conical tube for pre-processing bioburden testing. Using sterile forceps, the amniotic membrane was removed from the inner bag and placed in a sterile basin on a sterilely draped pre-set balance. The weight of the amniotic membrane was recorded. The sterile basin containing the amniotic membrane was transferred to a back table. Approximately 250 mL of Plasma Lyte-A was added to a second sterile basin and covered with the corresponding sterile lid. Using sterile forceps, the amniotic membrane was removed from the first sterile basin and transferred to a sterile prep board where the membrane was spread flat. Using a sterile lap sponge, any remaining debris/blood was removed from the surface of both sides of the amniotic membrane. The amniotic membrane was subsequently transferred to a second sterile basin containing Plasma Lyte-A where the membrane was covered, labeled and transferred to a quarantine refrigerator.

Amniotic Fluid Preparation

Sterile pipettes and 50 mL sterile conical centrifuge tubes were transferred to a sterile field. The Nalgene jar was moved in a gentle swirling motion to ensure cells were equally dispersed throughout amniotic fluid prior to removal of samples. The Nalgene jar containing the amniotic fluid was opened, and 10 mL of amniotic fluid was aspirated out utilizing a sterile pipette and transferred to a sterile conical tube for pre-processing bioburden testing. Approximately one mL of amniotic fluid was aspirated out utilizing a sterile pipette in order to complete the cell count. Utilizing a sterile 50 mL pipette, the remaining amniotic fluid was aseptically aspirated out of the Nalgene jar and transferred into 50 mL conical centrifuge tubes. Aliquots of the amniotic fluid were aseptically distributed in equal amounts in an even number of 50 mL sterile conical centrifuge tubes.

Batch Volume and Aliquot Fill Calculation

The batch volume and aliquot fill calculations (See FIG. 2) were determined based on the following calculations.
1. Record Amnion Weight (AW) in grams.
2. Calculate Amnion Allowable Aliquots (AA).
   2.1 Divide Amnion Weight (AW) by minimum starting amnion gram weight per 1 mL aliquot (0.03 grams) to calculate total Amnion Allowable Aliquots (AA).
3. Calculate Cell Count
   3.1 Record the total Amniotic Fluid Volume (A) in mL.
   3.2 Record the Total Cells Counted (B) for the four large corner squares and the middle square of the hemocytometer counting grid using the hemocytometer and an inversion microscope per standard operating procedures.
   3.3 Calculate Average Cells/Square (C).
      3.3.1 (C)=Total Cells Counted (B)/5 Squares Counted
   3.4 Record Dilution Factor used in preparation of cell count (D).
   3.5 Calculate the Total Cell Density (cells/mL) (E).
      3.5.1 (E)=(C)×(D)×$10^4$
   3.6 Calculate Total Cells (TC).
      3.6.1 Total Cells (TC)=Total Cell Density (E)×Total Volume of Amniotic Fluid (A)
4. Calculate Aliquot Cell Density (CD) (Aliquot=1 mL).
   4.1 (CD)_mL=Total Cell (TC)/Amnion Allowable Aliquot (AA)
5. Determine Bulk Product Volume (BV).
   5.1 (AA) Amnion Allowable Aliquots=Bulk Product Volume (BV)
6. Determine Lot Vial Fill Calculations.
   6.1 Record Bulk Product Volume (BV)
   6.2 Record the target vial production per size provided by management.
   6.3 Calculate Total Vial Target
   6.4 Calculate Total Volume Requirement for Vial Target.
      6.4.1 [Vial Target for 0.25 mL vials]×0.25=Volume Requirement (mL) for 0.25 mL Vials
      6.4.2 [Vial Target for 0.50 mL vials]×0.50=Volume Requirement (mL) for 0.5 mL Vials
      6.4.3 [Vial Target for 1.25 mL vials]×1.25=Volume Requirement (mL) for 1.25 mL Vials
   6.5 Calculate Total Vial Fill Volume.
   6.6 Compare Bulk Product Volume to Total Vial Fill Volume requirement based on the production plan.
      6.6.1 Total Vial Fill Volume must be Bulk Product Volume (BV).
      6.6.2 Adjust vial targets accordingly.

Solutions Calculations

After obtaining the Bulk Product Volume (BV), the component volumes for the tissue suspension solution (i.e., amnion suspension solution) and the cell suspension solution were determined based on the following calculations (See FIG. 3).
1.0 Bulk Product Volume (mL) (BV)=Total Suspension Solution Volume (mL) (SS)
2.0 Calculate Cell Suspension Solution Volume (CS)
   2.1 (CS)=Total Suspension Solution Volume (SS)/2
   2.2 Calculate (CS) Component Volume(s) Required:
      2.2.1 Plasma Lyte-A Volume (mL)=(CS)×0.91
      2.2.2 Human Albumin 25% Solution Volume (mL)=(CS)×0.09
   2.3 Calculate Amnion Suspension Solution (AS)
      2.3.1 (AS)=Total Suspension Solution Volume (SS)/2
      2.3.2 Calculate (AS) Component Volume(s) Required:
         2.3.2.1 Plasma Lyte-A Volume (mL)=(AS)×0.44
         2.3.2.2 Human Albumin 25% Sol. Volume (mL)=(AS)×0.36
         2.3.2.3 Dimethyl Sulfoxide, USP Volume (mL)=(AS)×0.20

Solution Preparations

The following materials were transferred to the sterile field: (i) Human Albumin 25% Solution, Excipient, EU Grade; (ii) Plasma Lyte-A Injection (pH 7.4); and (iii) DMSO (dimethyl sulfoxide), USP. In separate 1 L sterile containers, the cell suspension solution and the amnion suspension solution were prepared based on the calculations obtained utilizing the solution calculations sheet set forth in FIG. 3. The amnion control rate freeze solution was prepared according to the directions as set forth in FIG. 3. The containers were labeled with respective solution names, lot numbers, and expiration dates and stored at 1-10° C. pending further use.

Aseptic Processing of Amniotic Fluid Composition

Amniotic fluid-filled conical tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of Plasma Lyte-A was added to each conical tube to re-suspend the pellet and increase the volume in each tube to approximately 20 mL. Each tube was placed on a vortex mixer for 3-5 seconds to fully re-suspend the pellets. The contents of the conical centrifuge tubes were subsequently combined, reducing the overall conical centrifuge tube number by half by quickly pouring the suspension from a first tube to a second tube, ensuring maximum transfer of cells during combination. The process was repeated until all remaining conical centrifuge tubes were combined, reducing the number of tubes by half. The remaining conical centrifuge tubes were aseptically transferred to an Eppendorf centrifuge and centrifuged at 400×g for 10 minutes at ambient temperature. At the completion of each cycle, the conical tubes were aseptically transferred back to the sterile field. Each conical centrifuge tube was checked by a processing technician to ensure a pellet had formed. The results were recorded in the batch record. The supernatant was removed and discarded using a sterile pipette, and a sufficient volume of cell suspension solution was added to each conical tube to re-suspend the pellet and increase the volume in each tube to approximately 20 mL. Each tube was placed on a vortex mixer for 3-5 seconds to fully re-suspend the pellets. Next, each suspension was quickly poured into the container of cell suspension solution to form the amniotic fluid composition. The amniotic fluid composition was stored in refrigerated temperatures at 1-10° C. until further processing.

Amnion Control Rate Freezing

The following materials were transferred to the sterile field: amnion (in Plasma Lyte-A solution); amnion control rate freeze solution; appropriately sized pipettes; sterile bowl; sterile forceps, sterile tray; and sterile spatula. The amnion was removed from Plasma Lyte-A solution and transferred to the amnion control rate freeze solution. After 30 minutes, the amnion was removed from the amnion control rate freeze solution and transferred to the sterile tray where it was cut into four equal sections. The tray with the sectioned amnion was aseptically transferred to a control rate freezer. A control rate freezer probe was placed near the center of the chamber, taking care not to contact any metal in the chamber. The control rate freezer was activated by selecting a pre-programmed cycle.

Amnion Morselization

The amnion was subjected to morselization by cryogenic milling by the procedures described herein. A Spex Freezer/Mill® was programmed to the following settings: grinding rate=12; cycles=3; pre-cooling time=5 minutes; grinding time=2 minutes; and intermediate cooling=2 minutes. Sterile, autoclaved milling cylinders, impactors and end-caps were placed in an ultra-low freezer for a minimum of 15 minutes in order to pre-cool the materials prior to use. The milling cylinders, impactor and end-caps were removed from ultra-low freezer and aseptically transferred to the sterile field. One end cap was inserted onto each cylinder. The amnion was subsequently removed from the control rate freezer. One amnion section was placed into each of the four cylinders. An impactor bar was placed inside each of the four cylinders. The second end-cap was secured onto each cylinder, sealing the four milling chambers. The milling chambers were placed into the Spex Freezer/Mill® one at a time and allowed to run for the aforementioned program settings. At the conclusion of each milling event, the chamber was removed and immediately aseptically transferred to a sterile field. Using a sterile extractor tool, an end cap was removed from each chamber. The impactor bar and milled amnion were quickly dispensed into a sterile bowl. A sterile spatula was used to remove any remaining milled amnion from the milling cylinder or end-caps. Approximately 100 mL of amnion suspension solution was added to the milled amnion in a sterile bowl. Once thawed, any remaining amnion was removed from the impactor using a sterile spatula. This milling procedure was repeated for each of the four milling chambers until all milled amnion was added to the amnion suspension solution, thereby forming the tissue suspension.

Bulk Tissue Product

A sterile 2 L Erlenmeyer flask was aseptically transferred to a back table. The tissue suspension (amnion suspended in the amnion suspension solution) and the amniotic fluid composition were aseptically poured into the 2 L Erlenmeyer flask. The flask was appropriately covered and labeled. Immediately thereafter, the flask was placed in a quarantine refrigerator at 1-10° C.

Vial Fill

The following materials were transferred to the sterile field: sterile pipettes; sterile cryovial racks; sterile cryovials; and bulk tissue product. The bulk tissue product was removed from the quarantine refrigerator and placed on cold packs on a sterilely draped mixer. A stir bar was aseptically added to the bulk tissue product. The cryovials were filled using a repeater pipette pre-set to target fill volume as indicated in the production plan. Immediately following fill and capping, each cryovial was inspected per quality control (QC) standard operating procedures. Any vials failing QC inspection were discarded per biohazard waste disposal standard operating procedures. The cryovials that passed QC inspection were placed in cryovial racks.

Bulk Tissue Product Cryopreservation

The cryovial racks were transferred to sterile racks and placed in a control rate freezer. A control rate freezer probe was placed near the center of the chamber, taking care not to contact any metal in the chamber. The control rate freezer was activated by selecting a pre-programmed cycle. Upon completion of each control rate freeze, each cryovial was inspected per QC standard operating procedures. Any vials failing QC inspection were discarded per biohazard waste disposal standard operating procedures. The cryovial racks were placed in sterile containers and transferred to a quarantine ultra-low freezer to await results of all lot release testing before final packaging. Representative samples from the beginning, middle, and end of the cryovial fill cycle were removed from the final product count for lot release testing, which included: bioburden testing, mycoplasma DNA by polymerase chain reaction, and bacterial endotoxin test (Limulus Ameboycte Lysate).

Packaging of Cryopreserved Bulk Tissue Product

Throughout packaging procedures, the cryovials containing bulk tissue product were exposed to ambient temperature for a time period of one minute or less. After lot release testing clearance, each cryovial was packaged into a sterile foil pouch using aseptic technique. Using an AccuSeal 540Plus sealer, each foil pouch was sealed following standard operating procedures. Following QC inspection, each pouch was packaged in an outer box and labeled with the unique tissue identification number assigned to the cryovial, which was designed to ensure the traceability of the tissue from receipt through clinical use, transfer or destruction. Each cryovial was stored at ultra-low temperatures (≤−65° C.) prior to transplantation. Final product vial sizes were 0.25 mL, 0.50 mL, and 1.25 mL.

Example 1

This example illustrates the application of a placental construct according to an embodiment of the present invention during medical treatment of a surgical wound.

Figure 4:
FIG. 4 provides a photo of a post-surgical wound.

A 57 year old female presented with a history of osteoarthritis and underwent total right knee arthroplasty. FIG. 4 provides a photo of the post-surgery wound. The patient underwent a traditional course of various conservative methods of wound care, including weekly sharps debridement, enzymatic dressings, antimicrobial dressings, collagen dressing, and hyperbaric oxygen treatment to no avail for five months.

Figure 5:
FIG. 5 provides a photo of the post-surgical wound of FIG. 4 six weeks after treatment with a placental construct according to one embodiment.
Figure 6:
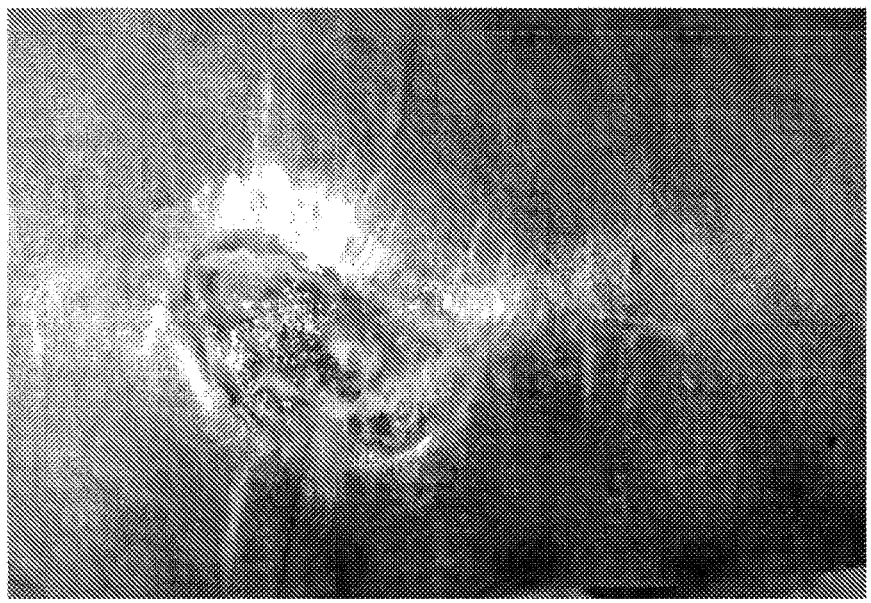
FIG. 6 provides a photo of the post-surgical wound of FIG. 4 fourteen weeks after treatment with a placental construct according to one embodiment.
Figure 7:
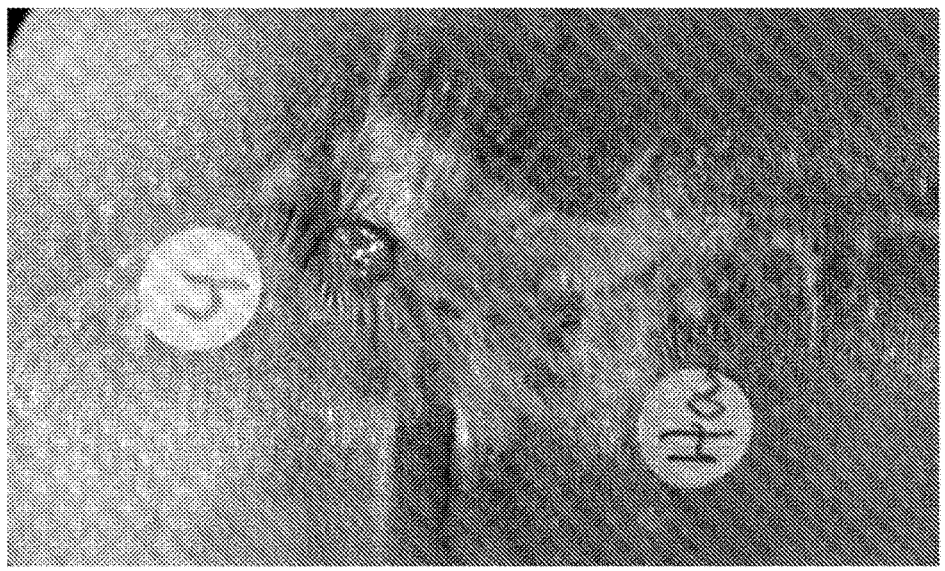
FIG. 7 provides a photo of the post-surgical wound of FIG. 4 twenty-one weeks after treatment with a placental construct according to one embodiment.

Pre-treatment measurements indicated a wound area of 33.5 sq. cm with a volume of 83.75 cm$^3$. The patient received standard wound prep cleansing and scrub of the affected area. The wound was debrided to the subcutaneous tissue, resulting in a bleeding wound bed which facilitated graft uptake. After irrigation and hemostasis, a placental construct as described herein was injected into the wound margins and amniotic membrane allografts were placed over the wound area. A hydrofiber silver impregnated dressing was fixed over the graft. The patient was given post treatment instructions to leave the dressing intact and to off-load the wound during ambulation. At weeks five and thirteen, a placental construct as described herein was injected into the wound margins and amniotic membrane allografts were placed over the wound area. The patient was seen weekly to assess wound margins. No evidence of infection, drainage, or adverse events was observed during the post-treatment follow up visits described herein. At week one, the patient exhibited 100% graft uptake with no evidence of membrane sloughing. At week two, the mean wound area was 29.7 sq. cm and the volume was 23.8 cm$^3$, providing a 72% closure rate. At week two, tissue granulation was visible with no signs of infection. The wound margins showed significant and rapid wound healing with optimal wound bed granulation. At week six, the mean wound area was 24.8 sq. cm and the volume was 12.4 cm$^3$, providing an 85% closure rate after two treatment applications (See FIG. 5). At week fourteen, the mean wound area was 14.4 sq. cm and the volume was 7.2 cm$^3$, providing a 91% closure rate after three treatment applications (See FIG. 6). At week twenty-one, the mean wound area was 1.6 sq. cm and the volume was 0.2 cm$^3$, providing a 99% closure rate (See FIG. 7).

As demonstrated, use of the placental construct in conjunction with an amniotic membrane allograft wound covering resulted in a significant and rapid enhancement in wound healing, significant tissue granulation formation, and no signs of infection.

Example 2

This example illustrates the application of a placental construct according to an embodiment of the present invention for the peri-implant regeneration of a failing dental implant.

A 71 year old male was referred for evaluation and treatment of a dental implant in dental site number 19 (Universal Tooth Numbering System) with bone loss and inflammation. Dental site number 20 was also a dental implant. Both implants had been placed several years prior. The two implants presented without crowns but the abutments were in place. The number 19 implant had a 9 mm periodontal probing depth on the distal-facial with bleeding on probing, no attached tissue on the facial and no detectable mobility. The number 20 implant had no detectable signs of inflammation, bone loss or mobility. Treatment was performed under local anesthesia and IV conscious sedation.

Figure 8:
FIG. 8 provides a photo of a dental surgical site after surgery to repair two dental implants using the placental construct according to one embodiment.

Full thickness flaps were reflected around the number 19 implant to gain access. The area was debrided with hand instruments and ultrasonics. A mandibular bone depression moat defect was detected around the number 19 implant. The intraboney defect was then grafted with freeze-dried bone allograft mixed with platelet rich plasma and the placental construct as described herein. Alloderm soft tissue allograft saturated with platelet rich plasma and the placental construct was laid over the defect, extending down on the facial between the bone and reflected periosteum. The site was sutured with 5-0 ePTFE suture. The post-surgical site is shown in FIG. 8.

Figure 9:
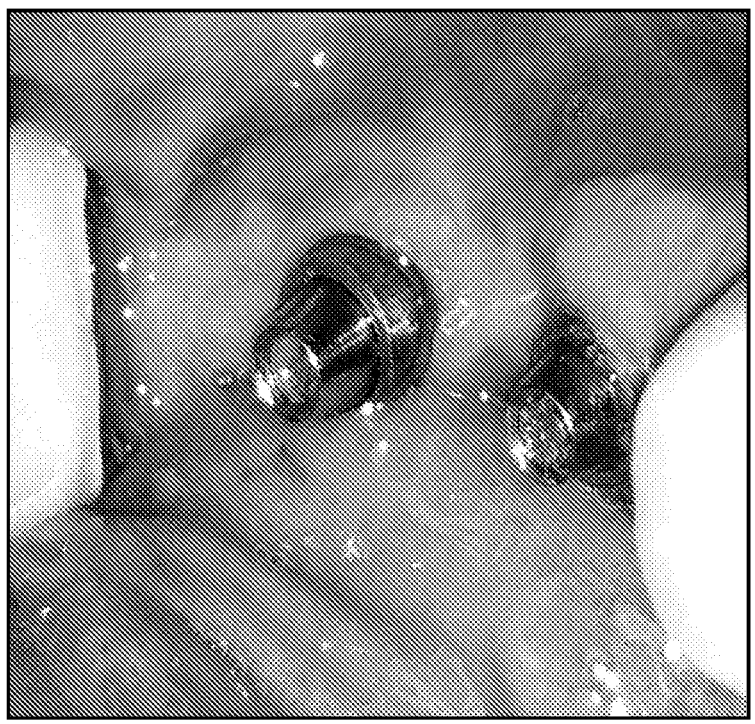
FIG. 9 provides a photo of the surgical site of FIG. 8 three months after treatment with a placental construct according to one embodiment.

The patient was seen at one week for a post-surgery appointment. The patient reported minimal discomfort and the sutures were left in place. At two weeks post-surgery, the patient was seen again and the sutures were removed. The patient reported minimal discomfort. At three months post-surgery (See FIG. 9), the number 19 implant probed 3-4 mm with no bleeding on probing. The soft tissue around number 19 healed uneventfully and appeared to gain in thickness and attached tissue. After three months post-surgery, the probing depth around number 19 decreased 5-6 mm and the gingival inflammation was not detectable. Radiographic bone gain was noticed at the third month. After the three month evaluation, the patient was referred back to his restorative dentist for the final restorations on numbers 19 and 20.

The combination of periodontal surgery, placental construct, platelet rich plasma, freeze-dried bone allograft and a soft tissue allograft yielded boney regeneration around an implant with vertical bone loss.

Example 3

This example illustrates the application of a placental construct according to an embodiment of the present invention during medical treatment of lateral epicondylitis (tennis elbow).

The patient was a 36 year old female with a history of chronic lateral epicondylitis of the right elbow, including pain in her upper right arm and joint. The patient was treated with conservative measures including physical therapy and medications. The patient had undergone a battery of tests including determination of clinical signs and symptoms, X-rays to rule out fractures and/or arthritis and ultrasound to determine the final diagnosis. The patient's pain was at a level of 9 (on a pain scale of 1-10). Given the mechanical evidence and findings of her clinical signs/symptoms and radiographic evidence, the patient elected to undergo a surgical procedure to correct the epicondylitis. A modified Bosworth surgical procedure was performed and included debridement of the extensor communis and the extensor carpi radialis brevis, partial lateral epicondylectomy, repair of the tendon, and injection of the placental construct as described herein.

Monthly follow-up visits were planned and the patient was monitored for healing and/or complications. Four weeks post-surgery, the patient reported pain at a level of 0 (on a pain scale of 1-10), but had not yet achieved full extension; however, the extension was significantly better than before the surgical procedure. The patient was instructed to continue full extension exercises. Eleven weeks post-surgery, the patient reported a pain level of 0 and had achieved full extension. The patient was instructed to continue full extension exercises. There were no complications reported throughout the post-surgery period.

Example 4

This example illustrates the application of a placental construct according to an embodiment of the present invention during a multiple level posterior spine reconstruction (instrumentation removal and revision) from T3-L4 vertebrae.

The patient was a 51 year old male with a history of right total hip replacement and recurrent and chronic spine pain which resulted in revision reconstructive surgery of the thoracolumbar spine from T8-L4. The patient improved with regard to resolution of his radiculopathy until increasing pain involving the mid and upper thoracic spine was experienced during exercise. The patient also noted significant compromise in the ability to stand in erect upright posture and reported activity-related numbness involving the lower extremities. The patient was treated with physical therapy and a conditioning/strengthening program with no significant improvement. The patient had undergone imaging that demonstrated a junctional kyphosis of approximately 20 degrees at the upper level of his surgery that corresponded to T7-T8. Endplate fracture at the inferior aspect of the T7 verterbral body with disk space narrowing was noted. Given the mechanical evidence and findings of his junctional kyphosis adjacent to the thoracic spine, the patient elected to undergo revision reconstructive surgery of the thoracic spine to address the junctional kyphotic deformity and to restore stability to the spine. The surgery extended from T3 to the previous surgery at L4. A bilateral post lateral arthrodesis was performed as well. The reconstruction was performed utilizing miscellaneous hardware such as a pedicle screw rod construct along with autogenous bone graft and demineralized cancellous allograft soaked with a placental construct as described herein. Demineralized bone matrix putty was also utilized in the reconstruction.

Monthly follow-up visits were planned and the patient was monitored for healing and/or complications. The first month post-surgery, a full spine X-ray was performed which demonstrated anatomic placement of the pedicle screw rod construct at T3-L4. The X-ray also showed correction of the junctional kyphotic deformity at T7-T8. Satisfactory sagittal and coronal balance was noted. Arthrodesis at the level of the surgical site was immature at this juncture. At three months post-surgery, a full spine X-ray was performed which demonstrated anatomic placement of the pedicle screw rod construct at T3-L4. The most cephalad aspect of his surgery at T3 revealed that the pedicle screw was parallel to the end plate. There was no evidence of any breakout or pullout or lucencies around the T3 pedicle screw (appeared to be anatomically placed). Progressive incorporation of the patient's posterolateral arthrodesis throughout the level of his revision construction was noted.

At ten months post-surgery, a full spine X-ray was performed which demonstrated that the cephalad screw and rod construct appeared to be in anatomic placement. There were mild degenerative changes at the adjacent level cephalad to the spinal reconstruction, namely corresponding to the T2-3 interspace. There was some reactive bone anterior to this space. However, there was no evidence of any junctional kyphotic deformity at that level. Mature incorporation of the posterolateral arthrodesis throughout the level of his revision construction was noted. There were no complications reported throughout the post-surgery period.

The placental construct as described herein, when used in the bone void treatment, created an environment that utilized the placental construct's osteogenic properties. The osteogenic properties, when combined with the osteoinductive ability of the autograft and the osteoconductive ability of the allograft, provided accelerated healing to form a solid posterolateral arthrodesis.

Example 5

This example illustrates the application of a placental construct according to an embodiment of the present invention during an anterior disc excision, decompression, interbody fusion and anterior fixation from L5-S1 vertebrae.

The patient was a 57 year old female with a history of intermittent problems in the lower back including paresthesias in both upper extremities, increasing pain in the lower back and lateral hip and pain extending over the anterior aspect of the left thigh. The patient was treated with physical therapy and a conditioning/strengthening program with no significant improvement. Diagnostic studies included X-rays of the cervical spine, X-rays of the lumbosacral spine, MRI scan of the lumbosacral spine and MRI scan of both hips. X-rays of the lumbosacral spine showed mild right-sided lumbar curve on the recumbent view, significant disc space narrowing with marginal hypertrophic change at L5-S1 with at least a moderate degree of associated facet hypertrophy, and some suggestion of increased density in the ilium adjacent to the left mid sacroiliac joint. The open lumbar MRI scan showed advanced degenerative changes at L5-S1, slight retrolisthesis of L5 on S1, severe disc space narrowing, endplate reactive changes and posterior osseous disc complex. Additionally, the MRI scan showed associated significant bilateral facet hypertrophy, which resulted in at least a moderate degree of bilateral recess narrowing and more market bilateral neuroforaminal narrowing. The canal was relatively shallow on a congenital basis and the central canal measured 5-6 mm at L5-S1. Also noted was a small left-sided facet joint cyst and facet joint effusion. Given the mechanical evidence and findings of the degenerative changes, the patient elected to undergo reconstructive surgery of the lumbosacral spine at L5-S1. Reconstruction surgery was performed utilizing a Vault implant and miscellaneous hardware as well as two demineralized cancellous allograft blocks soaked with the placental construct as described herein.

Monthly follow-up visits were planned and the patient was monitored for healing and/or complications. The first month post-surgery, a lumbosacral X-ray was performed which demonstrated that the anterior interbody implant was positioned well. Alignment was satisfactory with restoration of normal lumbosacral lordosis. There was no evidence of implant loosening or failure. At three months post-surgery, a lumbosacral X-ray was performed which demonstrated that the anterior instrumentation and implant appeared to be secure. There was evidence of further bony incorporation of the interbody fusion. At thirteen months post-surgery, a lumbosacral X-ray was performed which demonstrated that the interbody implant appeared to be secure at L5-S1 and there appeared to be a mature interbody fusion. There were no significant interval changes at the adjacent levels.

The placental construct as described herein, when used in the bone void treatment, created an environment that resulted in the formation of high density bone and enhanced the body's regenerative process after surgery even in the absence of the osteoinductive properties of local bone or blood. The surgery had a successful outcome including no complications and a timely interbody fusion.

Example 6

This example illustrates the application of a placental construct according to an embodiment of the present invention during a reconstructive surgery of the lumbosacral spine at L4-S1.

The patient was a 47-year-old female with primary symptoms of lower back pain and bilateral leg pain with weakness. The symptoms also included a degree of constant pain both in the lower back as well as the anterior and posterior aspect of both lower extremities. Back and leg symptoms were exacerbated during attempts at exercise and during prolonged periods of sitting, standing, walking, bending forward or backward, coughing, lifting, pushing and pulling. The patient was treated with a traditional course of various conservative measures including activity modification, medication, physical therapy, and chiropractic care. Diagnostic studies included X-rays of the lumbar spine, MRI scan of the lumbosacral spine and MRI scan of both hips. X-rays of the lumbosacral spine showed mild disc narrowing at L3-4, L4-5 and L5-S1. There was relatively shortened pedicle structure on a congenital basis causing a relatively shallow spinal canal at L3-4 and L4-5. The lumbar MRI scan demonstrated disc desiccation at each level in the lumbar spine. There was mild posterior space narrowing at L4-5 and L5-S1. Relatively mild circumferential disc bulging with mild facet hypertrophy was noted at L1-2, L2-3 and L3-4. L4-5 showed more significant circumferential disc bulging with disc extrusion. There was significant bilateral facet hypertrophy. The combination of disc extrusion and facet hypertrophy had resulted in significant central canal and bilateral lateral recess stenosis. L5-S1 showed a three mm posterior bulge, moderate bilateral facet hypertrophy and bilateral neuroforaminal narrowing with some compression of the exiting L5 nerve roots bilaterally. Given the mechanical evidence and findings of the degenerative changes, the patient elected to undergo reconstructive surgery of the lumbosacral spine at L4-S1. The reconstruction surgery was performed utilizing miscellaneous hardware as well as demineralized cancellous allograft and autogenous bone graft material soaked with the placental construct as described herein.

Monthly follow-up visits were planned and the patient was monitored for healing and/or complications. The first month post-surgery, a lumbosacral X-ray was performed which demonstrated that the instrumentation remained in place, with no evidence of loosening. The alignment was satisfactory. The posterolateral bone graft appeared to be gradually incorporating. The interbody fusion graft was difficult to visualize at this juncture of healing. At three months post-surgery, a lumbosacral X-ray was performed which demonstrated identical results to the one month follow-up images. At seven months post-surgery, a lumbosacral X-ray was performed which demonstrated that the instrumentation remained in place. Alignment was satisfactory and there appeared to be mature interbody and posterolateral fusion at both L4-L5 and L5-S1. There were no complications reported throughout the post-surgery period.

The placental construct as described herein, when used in the bone void treatment, created an environment that utilized the placental construct's osteogenic properties. The osteogenic properties, when combined with the osteoinductive ability of the autograft and the osteoconductive ability of the allograft, provided accelerated healing to form a solid posterolateral fusion.

Example 7

This example illustrates the application of a placental construct according to an embodiment of the present invention during a cervical spine fusion.

The patient was a 45 year old female with primary symptoms of neck pain, right upper extremity pain with functional weakness and question of myelopathic symptoms. Upon initial evaluation, patient had some degree of constant pain and stiffness in the posterior aspect of the neck and constant numbness and paresthesia extending into the right arm and hand, particularly involving the middle finger of the right hand. A lesser degree of similar symptoms was noted in the left upper extremity. The neck and arm symptoms were easily exacerbated by the neck movements or strenuous use of the upper extremities. The history included two years of progressive neck pain and associated neurological symptoms. The patient was treated with a traditional course of various conservative measures including a course of oral steroids. Diagnostic studies included X-rays of the cervical spine and MRI scan of the cervical spine. X-Rays of the cervical spine showed normal anterior soft tissue shadows. The overall bony quality appeared to be normal. There was relative straightening of the cervical spine on the neutral lateral view. There was moderate disc space narrowing at C5-6 and at least mild disc space narrowing at C6-7. There was a mild degree of posterior marginal hypertrophic change at C5-6 which extended into the right uncovertebral joint region. There was no evidence of instability on the lateral flexion/extension views. The cervical MRI scan demonstrated significant disc derangement with stenosis at C5-6 and C6-7. A lesser of degree of incidental degenerative change was noted at other levels in the cervical spine and upper thoracic spine. At C5-6, there was a broad based central and left paracentral disc herniation. This measured 3-4 mm in anterior/posterior thickness, caused a moderate central canal stenosis with associated flattening and mild compression of the cervical cord. The central canal measured 5 mm. There was moderate left lateral recess and mild right lateral recess secondary to the herniation. At C6-7 was a central left paracentral and right paracentral disc herniation which measured 3-4 mm in thickness. This was somewhat more prominent on the right side. There was mild flattening and compression of the cervical cord. There was marked right-sided foraminal narrowing and at least moderate bilateral lateral recess narrowing secondary to the herniation. There was loss of the ventral cerebrospinal fluid space at both C5-6 and C6-7 secondary to the ventral herniations and cord compression at these levels. There did not appear to be an intrinsic signal changes within the cervical cord. Given the mechanical evidence and findings of the degenerative changes, the patient elected to undergo reconstructive surgery of the cervical spine at C5-6 and C6-7.

The reconstruction surgery was performed utilizing a Valeo C Implant System with miscellaneous hardware, in addition to crushed cancellous allograft material soaked with the placental construct as described herein. Monthly follow-up visits were planned and the patient was monitored for healing and/or complications.

The first month post-surgery, a cervical X-ray was performed which demonstrated the instrumentation remained in place, and the alignment was satisfactory. The interbody grafts and anterior plate were well-positioned. At three months post-surgery, a cervical X-ray was performed which demonstrated the same conclusions as the previous report. Additionally, the interbody cages remained well-positioned and showed stable incorporation with the adjacent endplates. At nine months post-surgery, a cervical X-ray was performed which demonstrated that the anterior plate fixation appeared secure, and the overall alignment was satisfactory. There did not appear to be any significant interval changes at the adjacent levels. The interbody implants appeared secure consistent with a stable fusion. There were no complications reported throughout the post-surgery period.

The placental construct as described herein, when used in the bone void treatment, created an environment that utilized the placental construct's osteogenic properties. The osteogenic properties, when combined with the osteoinductive ability of the autograft and the osteoconductive ability of the allograft, provided accelerated healing to form a solid posterolateral fusion.

Example 8

This example illustrates the application of a placental construct according to an embodiment of the present invention during medical treatment of a diabetic foot ulcer.

A 65 year old male presented with a two-year non-healing right foot diabetic ulcer. The patient was treated with a traditional course of various conservative methods of wound care over the course of two years to no avail. Four doctors had previously recommended amputation, which the patient had refused. The patient was in dialysis three times per week and in need of a kidney transplant; however, the diabetic ulcer had prevented the patient from being placed on a transplant list.

Figure 10:
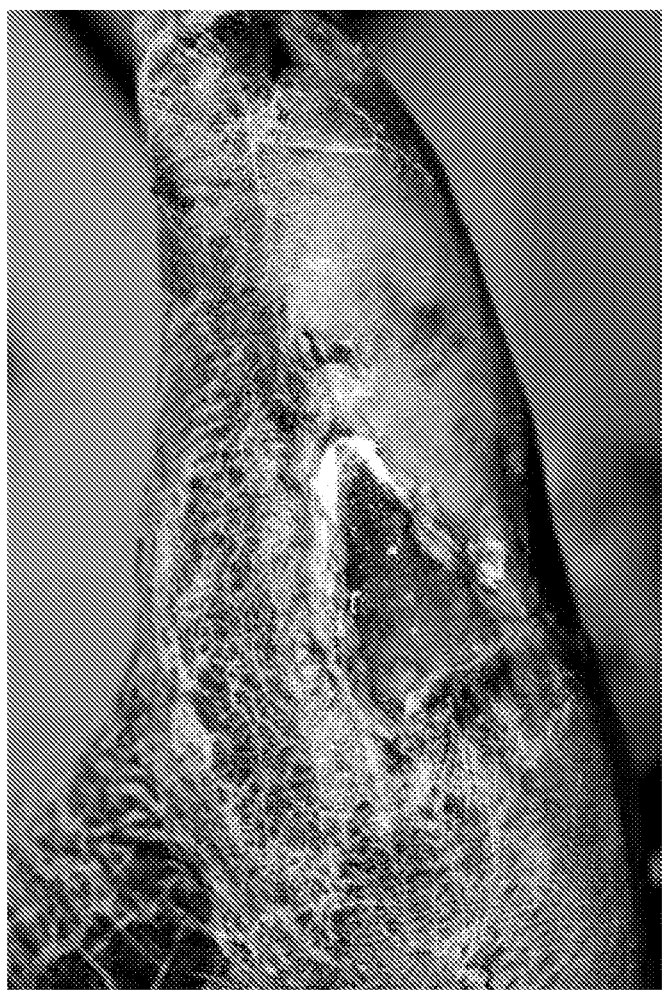
FIG. 10 provides a photo of a non-healing diabetic foot ulcer.

Prior to treatment with the placental construct, the wound measured 4.9 cm in length and 3.0 cm in width (wound volume=14.7 $cm^3$) with a deep sinus that posed a major threat to the foot (See FIG. 10). Severe lymphedema, avascularization and significant swelling were noted. The initial treatment involved ulcer debridement followed by application of two 1.25 mL of the placental construct as described herein diluted with saline 1:1 and injected around the ulcer margin at seven unique points. One 1.25 mL of the placental construct was diluted with 1:1 and applied topically. A dry wound covering was applied, and the wound was wrapped with gauze. Weekly follow-up visits were planned and the patient was monitored for healing and/or complications.

On day five following initial treatment, the wound measured 4.1 cm in length and 2.6 cm in width (wound volume=10.66 $cm^3$) with a deep sinus that posed a major threat to the foot. The measurements demonstrated a 28% closure rate. Inflammation reduction was noted, in addition to infiltration of healthy tissue to the deep sinus.

On day twelve following initial treatment, the wound measured 3.8 cm in length and 2.2 cm in width (wound volume=8.36 $cm^3$). Revascularization and healthy tissue fill-in of the deep sinus were noted. The wound treatment included ulcer debridement and application of two 2×2 cm amniotic membrane wound coverings with a Telfa, Tegaderm and a gauze wrap.

On day 21 following initial treatment, the wound measured 2.5 cm in length and 1.7 cm in width (wound volume=4.25 $cm^3$). The measurements demonstrated a 71% closure rate. Further, below knee swelling was reduced; visible ankle structure, skin tone, vascularity and color each improved; significant epithelialization was observed; and the deep sinus was closed.

Figure 11:
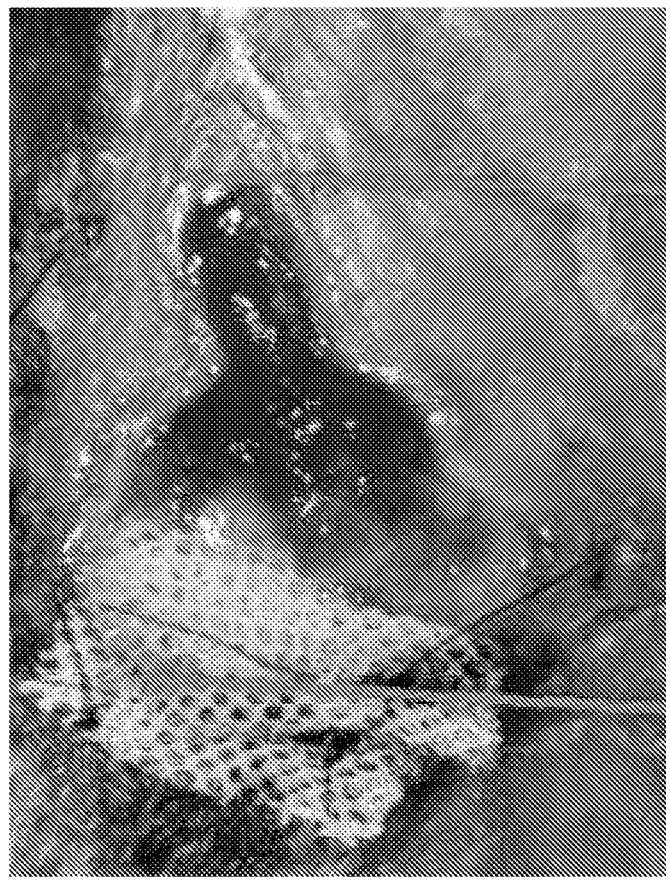
FIG. 11 provides a photo of the diabetic foot ulcer site of FIG. 10 twenty-eight days after treatment with a placental construct according to one embodiment.

On day 28 following initial treatment, the wound measured 2.3 cm in length and 1.7 cm in width (wound volume=3.9 $cm^3$). The measurements indicated a 74% closure rate (See FIG. 11). Day 28 treatment included minor debridement and injection of one 1.25 mL of the placental construct diluted with saline 1:1 around the ulcer margin at seven unique points. One 4×4 cm amniotic membrane wound covering was applied topically. A Telfa, non-porous cover, and Coban wrap were applied. Improved color and revascularization and reduction of inflammation were observed.

Figure 12:
FIG. 12 provides a photo of the diabetic foot ulcer site of FIG. 10 sixty-three days after treatment with a placental construct according to one embodiment.

Treatment on day 50 involved minor debridement and injection of one 1.25 mL of the placental constructed diluted with saline 1:1 around the ulcer margin at seven unique points. On day 63 following initial treatment, the wound was closed (See FIG. 12). The patient was last seen on day 235. Improved revascularization, color and tone were noted. The wound remained closed. There were no complications reported throughout the post-treatment period.

Example 9

This example illustrates the application of a placental construct according to an embodiment of the present invention during medical treatment of a cutaneous ulcer.

A 62 year old female presented with a single right foot bunion ulcer. The patient had a history of peripheral neuropathy and osteomyelitis at the right metatarsal near the right foot bunion ulcer. The patient was treated with a traditional course of various conservative methods of wound care over the course of one year to no avail. Prior to treatment with the placental construct, wound measurements were noted. The initial treatment involved minor ulcer debridement and injection of one 1.25 mL of the placental construct as described herein diluted with saline 1:1 around the ulcer margin and into the wound bed. Telfa and a non-porous wound covering were applied with a Coban wrap. An osteomyelitis defect measuring 5.42 mm was detected on X-ray. Weekly follow-up visits were planned and the patient was monitored for healing and/or complications.

Figure 13:
FIG. 13 provides a photo of a bunion ulcer site eight days after treatment with a placental construct according to one embodiment.
Figure 14:
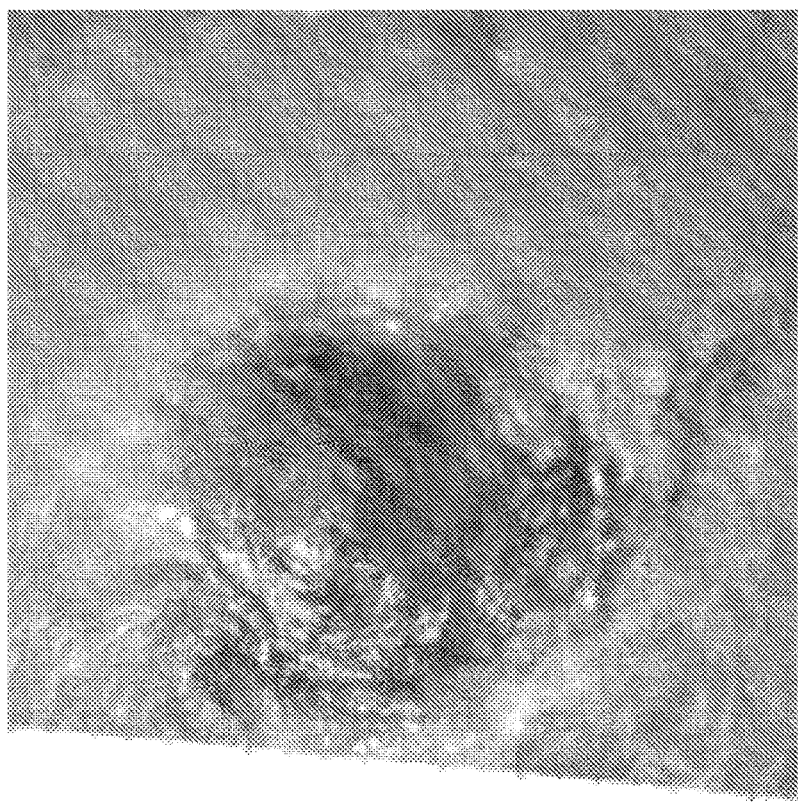
FIG. 14 provides a photo of a bunion ulcer site fifteen days after treatment with a placental construct according to one embodiment.
Figure 15:
FIG. 15 provides a photo of a bunion ulcer site seventy days after treatment with a placental construct according to one embodiment.

On day eight following initial treatment, the wound measured 1.4 cm in length and 1.4 cm in width (wound volume=1.96 $cm^3$) (See FIG. 13). These measurements were the first noted. On day 15 following initial treatment, the wound measured 1.1 cm in length and 1.2 cm in width (wound volume=1.32 $cm^3$). The measurements demonstrated a 33% closure rate (See FIG. 14). On day 22 following initial treatment, the wound measured 1.1 cm in length and 0.9 cm in width (wound volume=0.99 $cm^3$). The measurements demonstrated a 51% closure rate. The beginning of osteomyelitis resolution was noted (defect measured 4.56 mm). On day 36 following initial treatment, the wound measured 0.7 cm in length and 0.7 cm in width (wound volume=0.49 $cm^3$). The measurements demonstrated a 75% closure rate. On day 36, treatment involved injection of one 1.25 mL of the placental construct diluted with saline 1:1 around the right foot bunion ulcer. A Telfa, non-porous cover and Coban wrap were applied. On day 48 following initial treatment, the wound measured 0.6 cm in length and 0.5 cm in width (wound volume=0.3 cm³). Some osteomyelitis resolution was noted (defect measured 4.41 mm). On day 70, the wound was closed (See FIG. 15) with complete osteomyelitis resolution. No complications were reported throughout the post-treatment period.

I claim:

1. A method of treating a soft tissue defect in or on the body of a patient comprising the steps of:
providing a placental construct comprising: i) a therapeutically effective amount of a human birth tissue material that is cryofrozen, morselized and subsequently suspended in a tissue suspension solution; and ii) an amniotic fluid composition; and
administering the placental construct directly into or onto the soft tissue defect,
wherein the tissue suspension solution comprises about 36% volume of human albumin 25% solution and about 20% volume of dimethyl sulfoxide.

2. The method of claim 1, wherein the soft tissue defect is a diabetic ulcer, decubitus ulcer, venous leg ulcer, arterial leg ulcer, cutaneous ulcer, or a combination thereof.

3. The method of claim 1, wherein the construct further comprises one or more structural carriers selected from the group consisting of an amniotic membrane and/or chorionic membrane, a soft tissue allograft, a bone allograft, and platelet rich plasma.

4. The method of claim 1, wherein the construct is administered in combination with one or more bioactive agents selected from the group consisting of physiologically compatible minerals, growth factors, antibiotics, chemotherapeutic agents, antigens, antibodies, enzymes, vectors for gene delivery, and hormones.

5. A method of treating a soft tissue defect in or on the body of a patient comprising the step of
administering a placental construct directly into or onto the soft tissue defect, wherein the placental construct comprises a therapeutically effective amount of a human birth tissue material comprising a tissue suspension and an amniotic fluid composition, the human birth tissue material prepared according to a process comprising the steps of:

(a) recovering placental tissue components and amniotic fluid from a single seronegative, healthy human via cesarean section or vaginal delivery;
(b) subjecting the placental tissue components to cryopreservation;
(c) morselizing the cryopreserved placental tissue components;
(d) homogenizing the morselized placental tissue components in a tissue suspension solution to form a tissue suspension;
(e) centrifuging the amniotic fluid from step (a) to form a pellet that is retained and a supernatant that is aspired off;
(f) suspending the pellet in a cell suspension solution to form an amniotic fluid composition;
(g) homogenizing the tissue suspension from step (d) with the amniotic fluid composition of step (f) to form a bulk tissue product; and
(h) cryofreezing the bulk tissue product to form the human birth tissue material;
wherein the tissue suspension solution comprises about 36% volume of human albumin 25% solution and about 20% volume of dimethyl sulfoxide.

6. The method of claim 5, wherein the soft tissue defect is a diabetic ulcer, decubitus ulcer, venous leg ulcer, arterial leg ulcer, cutaneous ulcer, or a combination thereof.

7. The method of claim 5, wherein the construct further comprises one or more structural carriers selected from the group consisting of an amniotic membrane and/or chorionic membrane, a soft tissue allograft, a bone allograft, and platelet rich plasma.

8. The method of claim 5, wherein the construct is administered in combination with one or more bioactive agents selected from the group consisting of physiologically compatible minerals, growth factors, antibiotics, chemotherapeutic agents, antigens, antibodies, enzymes, vectors for gene delivery, and hormones.

* * * * *